US009427388B2

(12) United States Patent
Ino

(10) Patent No.: US 9,427,388 B2
(45) Date of Patent: Aug. 30, 2016

(54) CLEANSING AGENT COMPOSITION COMPRISING SULFONATE-TYPE SURFACTANT AND/OR SULFATE-TYPE ANIONIC SURFACTANT AND HETEROCYCLIC COMPOUND

(71) Applicant: AJINOMOTO CO., INC., Tokyo (JP)

(72) Inventor: Masahiro Ino, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/664,965

(22) Filed: Mar. 23, 2015

(65) Prior Publication Data

US 2015/0190325 A1 Jul. 9, 2015

Related U.S. Application Data

(63) Continuation of application No. PCT/JP2013/075770, filed on Sep. 24, 2013.

(30) Foreign Application Priority Data

Sep. 24, 2012 (JP) ................................ 2012-209728

(51) Int. Cl.

| | | |
|---|---|---|
| C11D 1/12 | (2006.01) | |
| C11D 3/28 | (2006.01) | |
| C11D 3/20 | (2006.01) | |
| A61K 8/49 | (2006.01) | |
| C11D 1/28 | (2006.01) | |
| C11C 1/06 | (2006.01) | |
| C11D 1/29 | (2006.01) | |
| C11D 1/04 | (2006.01) | |
| A61Q 19/10 | (2006.01) | |
| A61K 8/46 | (2006.01) | |
| A61K 8/34 | (2006.01) | |
| A61K 8/81 | (2006.01) | |
| A61K 8/92 | (2006.01) | |
| A61Q 5/02 | (2006.01) | |

(52) U.S. Cl.

CPC .............. *A61K 8/494* (2013.01); *A61K 8/345* (2013.01); *A61K 8/463* (2013.01); *A61K 8/466* (2013.01); *A61K 8/8147* (2013.01); *A61K 8/92* (2013.01); *A61Q 5/02* (2013.01); *A61Q 19/10* (2013.01); *C11C 1/06* (2013.01); *C11D 1/04* (2013.01); *C11D 1/12* (2013.01); *C11D 1/28* (2013.01); *C11D 1/29* (2013.01); *C11D 3/28* (2013.01)

(58) Field of Classification Search

CPC ............. C11D 1/04; C11D 1/06; C11D 1/12; C11D 1/28; C11D 1/29; C11D 3/28

USPC ....... 510/127, 130, 136, 137, 138, 477, 488, 510/500, 505, 506

See application file for complete search history.

(56) References Cited

U.S. PATENT DOCUMENTS

| | | | |
|---|---|---|---|
| 5,328,630 A | 7/1994 | Nozaki et al. | |
| 5,879,409 A * | 3/1999 | Kott ..................... | C11D 3/3947 252/186.39 |
| 6,096,098 A * | 8/2000 | Miracle ................ | C11D 3/3917 252/186.27 |
| 7,820,146 B2 * | 10/2010 | Ferrari .................. | A61K 8/891 424/401 |
| 2002/0042354 A1 | 4/2002 | Lang et al. | |
| 2004/0170586 A1 * | 9/2004 | Ferrari .................. | A61K 8/31 424/63 |
| 2005/0180939 A1 | 8/2005 | Fonolla Moreno | |
| 2006/0239952 A1 | 10/2006 | Hattori | |
| 2010/0135917 A1 | 6/2010 | Winter et al. | |
| 2014/0308879 A1 * | 10/2014 | Yoshida ................ | B24B 37/044 451/41 |

FOREIGN PATENT DOCUMENTS

| | | |
|---|---|---|
| EP | 1 672 055 A1 | 6/2006 |
| JP | 5-156281 A | 6/1993 |
| JP | 2002-504948 A | 2/2002 |
| WO | WO 2007/017441 A1 | 2/2007 |
| WO | WO 2011/118340 A1 | 9/2011 |

OTHER PUBLICATIONS

Extended European Search Report issued Feb. 26, 2016 in Patent Application No. 13838984.6.

* cited by examiner

*Primary Examiner* — Gregory R Delcotto
(74) *Attorney, Agent, or Firm* — Oblon, McClelland, Maier & Neustadt, L.L.P.

(57) ABSTRACT

A cleansing agent composition containing
(A) a sulfonate-type surfactant and/or a sulfate-type anionic surfactant, and
(B) a heterocyclic compound represented by the formula (1)

(1)

$$\begin{array}{c}\text{O}\end{array}\underset{\underset{\text{H}}{\big|}}{\overset{\underset{\text{H}}{\big|}}{\text{N}}}\text{R}^1$$
$$\text{R}^2\underset{\underset{\text{H}}{\big|}}{\overset{}{\text{N}}}\text{O}$$

wherein $R^1$ and $R^2$ are each independently a hydrogen atom, a methyl group, a hydroxymethyl group, or a hydroxyethyl group, shows high detergency and low irritativeness, can suppress rough skin after washing and drying, and can be preferably used for cosmetic agents.

20 Claims, No Drawings

CLEANSING AGENT COMPOSITION COMPRISING SULFONATE-TYPE SURFACTANT AND/OR SULFATE-TYPE ANIONIC SURFACTANT AND HETEROCYCLIC COMPOUND

CROSS REFERENCES TO RELATED APPLICATIONS

This application is a continuation of International Patent Application No. PCT/JP2013/075770, filed on Sep. 24, 2013, and claims priority to Japanese Patent Application No. 2012-209728, filed on Sep. 24, 2012, all of which are incorporated herein by reference in their entireties.

BACKGROUND OF THE INVENTION

1. Field of the Invention

The present invention relates to a cleansing agent composition containing a sulfonate-type surfactant and/or a sulfate-type anionic surfactant, and a specific heterocyclic compound.

2. Discussion of the Background

Cleansing agent compositions for skin and hair generally contain an anionic surfactant as a main component. To avoid irritation of fatty acid salt used in alkaline, sulfonate-type surfactants such as sulfosuccinate-type, isethionate-type and the like, or sulfate-type anionic surfactants are widely used.

However, cleansing agent compositions containing these anionic surfactants as main components are superior in detergency but pose problems in terms of sense of use as evidenced by rough skin after washing and drying and the like. Furthermore, when a sulfate-type anionic surfactant is used, the problem of irritativeness to the skin still remains.

In view of the above, a cleansing agent composition containing, as a main component, a surfactant other than anionic surfactants, a cleansing composition using a reduced amount of the anionic surfactant itself combined with other surfactant, and the like have been developed (e.g., patent document 1). However, they often fail to show inherent detergency, and have many restrictions on formulation to improve the detergency. Therefore, a sufficiently satisfactory cleansing agent composition is difficult to obtain.

DOCUMENT LIST

Patent Document patent document 1: JP-A-5-156281

SUMMARY OF THE INVENTION

Problems to be Solved by the Invention

Accordingly, an object of the present invention is to provide a cleansing agent composition having high detergency, which shows low irritativeness and good sense of use such as being free of rough skin after washing and drying and the like.

Means of Solving the Problems

As a result of intensive studies in such situation, it was found that a cleansing agent composition showing high detergency, low irritativeness and suppression of rough skin after washing and drying can be provided by adding a sulfonate-type surfactant and/or a sulfate-type anionic surfactant, and a heterocyclic compound having a particular structure in combination, which resulted in the completion of the present invention.

Accordingly, the present invention includes the following embodiments.

[1] A cleansing agent composition comprising
(A) a sulfonate-type surfactant and/or a sulfate-type anionic surfactant, and
(B) a heterocyclic compound represented by the formula (1)

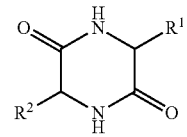

wherein $R^1$ and $R^2$ are each independently a hydrogen atom, a methyl group, a hydroxymethyl group, or a hydroxyethyl group.

[2] The cleansing agent composition of the above-mentioned [1], wherein $R^1$ and $R^2$ in the formula (1) are hydrogen atoms.

[3] The cleansing agent composition of the above-mentioned [1] or [2], wherein the sulfate-type anionic surfactant is an alkyl or alkenyl sulfate-type anionic surfactant.

[4] The cleansing agent composition of any one of the above-mentioned [1] to [3], wherein a weight ratio (A/B) of (A) the sulfonate-type surfactant and/or the sulfate-type anionic surfactant and (B) the heterocyclic compound in the cleansing agent composition is 1000/10-1000/1.

[5] The cleansing agent composition of any one of the above-mentioned [1] to [4], wherein a total amount of the components (A) and (B) is 5-95 wt % of the whole weight of the cleansing agent composition.

[6] The cleansing agent composition of any one of the above-mentioned [1] to [5], further comprising (C) a polyacryl acid or a derivative thereof.

[7] The cleansing agent composition of any one of the above-mentioned [1] to [6], further comprising (D) an oil component and/or (E) polyol.

Effect of the Invention

The composition obtained by the present invention shows high detergency and low irritativeness, can suppress rough skin after washing and drying and, surprisingly, can confer softness and moisture to the skin after using and improve touch of skin after rinsing, and is superior in stability.

DETAILED DESCRIPTION OF THE PREFERRED EMBODIMENTS

The composition of the present invention contains (A) a sulfonate-type surfactant and/or a sulfate-type anionic surfactant, and (B) a particular heterocyclic compound.

[(A). Sulfonate-Type Surfactant and/or Sulfate-Type Anionic Surfactant]

Examples of the sulfonate-type surfactant for component (A) of the present invention include sulfosuccinate-type anionic surfactants, isethionate-type anionic surfactants and the like, and examples of the sulfate-type anionic surfactant include alkyl or alkenyl sulfate-type anionic surfactants and the like.

The sulfonate-type surfactant and the sulfate-type anionic surfactant may be used singly or may be used in combination.

As the sulfosuccinate-type anionic surfactant, the compounds represented by the following formula (2) and (3) can be mentioned.

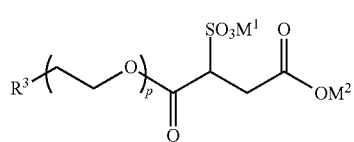
(2)

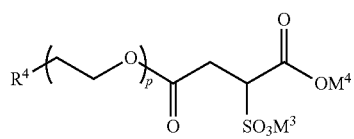
(3)

wherein $R^3$ and $R^4$ are each independently $R^5$—O— or $R^6$—CO—NH— ($R^5$ is a straight chain or branched chain alkyl group having 8-22 carbon atoms or a straight chain or branched chain alkenyl group having 8-22 carbon atoms, $R^6$ is a straight chain or branched chain alkyl group having 7-21 carbon atoms or a straight chain or branched chain alkenyl group having 7-21 carbon atoms), $M^1$, $M^2$, $M^3$ and $M^4$ are each independently a hydrogen atom or a cation forming a water-soluble salt, which is selected from an alkali metal, an alkaline earth metal, ammonium and organic ammonium, and p is 0-20, provided that both $M^1$ and $M^2$, and $M^3$ and $M^4$ are not simultaneously hydrogen atoms.

Examples of the straight chain or branched chain alkyl group having 8-22 carbon atoms include octyl, nonyl, decyl, undecyl, dodecyl (lauryl), tridecyl, tetradecyl (myristyl), pentadecyl, hexadecyl (palmityl, cetyl), heptadecyl, octadecyl (stearyl), nonadecyl, icosyl (arachidinyl), docosyl (behenyl) and the like.

Examples of the straight chain or branched chain alkyl group having 7-21 carbon atoms include heptyl, octyl, nonyl, decyl, undecyl, dodecyl (lauryl), tridecyl, tetradecyl (myristyl), pentadecyl, hexadecyl (palmityl, cetyl), heptadecyl, octadecyl (stearyl), nonadecyl, icosyl (arachidinyl) and the like.

Examples of the straight chain or branched chain alkenyl group having 8-22 carbon atoms include octenyl, nonenyl, decenyl, undecenyl, dodecenyl, tridecenyl, tetradecenyl (myristoleyl), pentadecenyl, hexadecenyl (palmitoleyl), heptadecenyl, octadecenyl (oleyl, vaccenyl), nonadecenyl, icosenyl (gadoleyl, eicosenyl), docosenyl (erucyl), octadecadienyl (linoleyl), icosadienyl (eicosadienyl, docosadienyl), octadecatrienyl (linolenyl) and the like.

Examples of the straight chain or branched chain alkenyl group having 7-21 carbon atoms include groups formed by removing a methylene group at the binding site from the above-mentioned "straight chain or branched chain alkenyl group having 8-22 carbon atoms".

Examples of the alkali metal include lithium, sodium, potassium and the like, examples of the alkaline earth metal include magnesium, calcium and the like, and examples of the organic ammonium include alkanolamine having 2 or 3 carbon atoms (ethanolamine, diethanolamine, triethanolamine basic amino acid (arginine, histidine, lysine etc.), ammonium such as diallyldimethylammonium chloride, PEG-5 stearylammonium chloride and the like.

Examples of the sulfosuccinate-type anionic surfactant represented by the above-mentioned formula (2) or (3) wherein $R^3$ and $R^4$ are $R^5$—O— include a disodium sulfosuccinate of secondary alcohol having 11-13 carbon atoms or its ethoxylate [manufactured by Nippon Shokubai Co., Ltd., softanol MES 3, 5, 7, 9, 12 etc. (each number shows average addition molar number (EC) of ethylene oxide)], a disodium sulfosuccinate of lauryl alcohol or lauryl alcohol ethoxylate (EO=3, 4, 6, 9, 12) (manufactured by TOHO Chemical Industry Co., Ltd., Kohakuru L-400 etc.), a disodium sulfosuccinate of synthetic primary alcohol having 12-15 carbon atoms or its ethoxylate (EO=2-12), a disodium sulfosuccinate of Guerbet alcohol having 8-22 carbon atoms or its ethoxylate (EO=2-12) and the like.

Examples of the sulfosuccinate-type anionic surfactant represented by the above-mentioned formula (2) or (3) wherein $R^3$ and $R^4$ are $R^6$—CO—NH— include a disodium salt of sulfosuccinate of lauric polyethylene glycol (EO=1, 2) amide, a disodium salt of sulfosuccinate of oleic polyethylene glycol (EO=1, 2) amide, a disodium salt of sulfosuccinate of polyethylene glycol (EO=4) amide of coconut oil fatty acid and the like.

The sulfosuccinate-type anionic surfactant to be used in the present invention may be used singly or may be used in combination. The above-mentioned sulfosuccinate-type anionic surfactant represented by the above-mentioned formula (2) or (3) wherein $R^3$ and $R^4$ are $R^5$—O— is more preferable. As $M^1$, $M^2$, $M^3$ and $M^4$, sodium, potassium, ammonium, alkanol ammonium, and ammonium of basic amino acid and the like are preferable.

As the isethionate-type anionic surfactant, the compound represented by the following formula (4) can be mentioned.

 (4)

wherein $R^7$ is a straight chain or branched chain alkyl group having 7-19 carbon atoms, a straight chain or branched chain alkenyl group having 7-19 carbon atoms or a straight chain or branched chain hydroxyalkyl group having 7-19 carbon atoms, and $M^5$ is an alkali metal or a cation forming a water-soluble salt of organic ammonium.

Examples of the straight chain or branched chain alkyl group having 7-19 carbon atoms include heptyl, octyl, nonyl, decyl, undecyl, dodecyl (lauryl), tridecyl, tetradecyl (myristyl), pentadecyl, hexadecyl (palmityl, cetyl), heptadecyl, octadecyl (stearyl), nonadecyl and the like, examples of the straight chain or branched chain alkenyl group having 7-19 carbon atoms include groups formed by removing a methylene group at the binding site from octenyl, nonenyl, decenyl, undecenyl, dodecenyl, tridecenyl, tetradecenyl (myristoleyl), pentadecenyl, hexadecenyl (palmitoleyl), heptadecenyl, octadecenyl (oleyl, vaccenyl), octadecadienyl (linoleyl), octadecatrienyl (linolenyl) and the like, and examples of the straight chain or branched chain hydroxyalkyl group having 7-19 carbon atoms include 11-hydroxyheptadecyl and the like.

Examples of the alkali metal include lithium, sodium, potassium and the like, examples of the organic ammonium include alkanolamine having 2 or 3 carbon atoms (ethanolamine, diethanolamine, triethanolamine etc.), basic amino acid (arginine, histidine, lysine etc.), ammonium such as diallyldimethylammonium chloride, PEG-5 stearylammonium chloride and the like.

In the above-mentioned formula (4), $C_{11}H_{23}COO$—, $C_{13}H_{27}COO$—, $C_{15}H_{31}COO$—, $C_{17}H_{35}COO$—, coconut oil fatty acid residue and the like can be specifically mentioned as $R^7COO$—, and lithium, potassium, sodium, monoethanolammonium, diethanolammonium, triethanolammonium and the like can be specifically mentioned as $M^5$.

As the alkyl or alkenyl sulfate-type anionic surfactant, alkyl or alkenylethersulfate, each of which has a straight chain or branched chain alkyl group having 10-20 carbon atoms or a straight chain or branched chain alkenyl group having 10-20 carbon atoms, and average 0.5-8 ethylene oxide, propylene oxide, butylene oxide added in one molecule, or ethylene oxide and propylene oxide added at a ratio of 0.1/9.9-9.9/0.1, or ethylene oxide and butylene oxide added at a ratio of 0.1/9.9-9.9/0.1, or alkyl or alkenylsulfate having an alkyl group or alkenyl group having 10-20 carbon atoms can be mentioned.

As the straight chain or branched chain alkyl group or alkenyl group having 10-20 carbon atoms, a straight chain or branched chain alkyl group or alkenyl group having 10-20 carbon atoms can be mentioned from those having 8-22 carbon atoms and recited as examples of $R^5$ and the like.

Specific examples of the alkyl or alkenyl sulfate-type anionic surfactant include sodium lauryl sulfate (manufactured by Kao Corporation, EMAL 0 etc.), sodium polyoxyethylene lauryl ether sulfate (manufactured by Kao Corporation, EMAL 20C) and the like.

The alkyl or alkenyl sulfate-type anionic surfactant may be used singly or may be used in combination.

[(B) Heterocyclic Compound]

The heterocyclic compound to be used as component (B) in the present invention shows the property of easy retention of water due to the polarity produced by the amide bond in a molecule, and a cleansing agent composition containing same shows an action to suppress rough skin after washing and drying and confers softness and moisture to the skin after using. In general, as compared to hydrocarbon compounds, many of the compounds having a polar group such as carboxyl group, hydroxy group and the like have water-absorbability, show good affinity for water and are used for moisturizers. However, a compound having two adjacent amide bonds, forming a 6-membered ring and superior in affinity for skin, like this product, has not been used for a cleansing agent.

The heterocyclic compound to be used as component (B) in the present invention is represented by the formula (1).

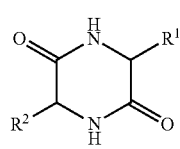
(1)

wherein $R^1$ and $R^2$ are each independently a hydrogen atom, a methyl group, a hydroxymethyl group or a hydroxyethyl group (1-hydroxyethyl group, 2-hydroxyethyl group). Preferably, it is a hydrogen atom, a hydroxymethyl group or a 1-hydroxyethyl group, more preferably, a hydrogen atom. A hydroxy group tends to increase polarity and enhance moisturizing-ability, as well as suppress rough skin after washing and drying. When it is an alkyl group having a larger carbon atom number such as ethyl group, propyl group and the like, solubility in water tends to decrease markedly, and foaming tends to decrease, whereby utilization as a cleansing agent composition becomes limited or difficult.

The heterocyclic compound represented by the formula (1) of the present invention can also be present as a tautomer represented by the following formula (1'), and can be mutually convertible. A tautomer represented by the formula (1') is also included in the present invention.

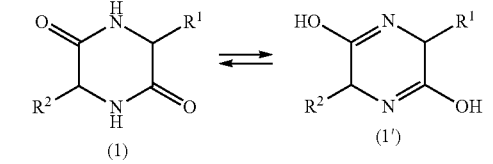

Also, when at least one of $R^1$ and $R^2$ is other than a hydrogen atom, the heterocyclic compound represented by the formula (1) can be present as a stereoisomer such as an optically active form, a diastereomer and the like. The stereoisomer may be used singly or may be used as a mixture thereof (racemate, diastereomer mixture etc.).

The heterocyclic compound represented by the formula (1) can be produced from a known optically active or racemic amino acid (glycine, alanine, serine, threonine etc.) by cyclic condensation by a method known per se, or a commercially available product can also be used.

The mixing ratio of component (A) and component (B) in the cleansing agent composition of the present invention in weight ratio is preferably A/B=1000/10-5000/1, more preferably A/B=1000/10-1000/1 and further more preferably 1000/5-1000/2.

While the total amount of component (A) and (B) varies depending on the dosage form of the cleansing agent composition, it is preferably 5-95 wt %, more preferably 5-50 wt %, further more preferably 5-30 wt %, of the whole weight of the composition.

In addition to the aforementioned property, the cleansing agent composition of the present invention shows improved touch of skin after rinsing by further adding polyacryl acid or a derivative thereof as component (C) to the composition.

Examples of the polyacryl acid or a derivative thereof include polyacrylic acid, polyacryl acid amide, methyl polyacrylate, ethyl polyacrylate, carboxyvinyl polymer, acrylic acid-methacrylic acid alkyl copolymer, ethyl acrylate-acrylic acid amide-acrylic acid copolymer, ethyl acrylate-ethyl methacrylate copolymer, butyl acrylate-methacrylic acid To copolymer, butyl acrylate-hydroxymethacrylic acid copolymer, methoxyethyl acrylate-hydroxyethyl acrylate copolymer and the like.

The polyacryl acid or a derivative thereof also include those wherein a part of or whole acid forms a salt. For example, alkali metal salt, alkanolamine salt having 2 or 3 carbon atoms, ammonium salt and the like can be mentioned, and sodium salt, potassium salt, ethanolamine salt, diethanolamine salt, and triethanolamine salt can be specifically mentioned.

The polyacryl acid or a derivative thereof may be used singly or a combination of two or more kinds thereof.

The molecular weight of the polyacryl acid or a derivative thereof is preferably within the range of 500,000-5,000,000, and the lower limit is preferably 800,000, more preferably 1,000,000 from the aspects of stability of the viscosity of formulation. The upper limit is preferably 4,500,000, more preferably 4,000,000, since addition is sometimes difficult due to the problem of solubility.

Polyacryl acid or a derivative thereof is desirably contained within the range of 0.05-2 wt % in the cleansing agent composition of the present invention. From the aspect of the improvement of the texture, the lower limit is more preferably 0.08 wt %, more preferably 0.1 wt %. Since stickiness is sometimes developed as a sense of use, the upper limit is preferably 1.5 wt %, more preferably 1 wt %.

The cleansing agent composition of the present invention can further confer moisturizability to the skin and improve stability of the composition by adding an oil component as component (D) and/or polyol as component (E) in combination. That is, separation and phase separation, precipitation and deposition of the solubilized components can be suppressed.

Component (D) and component (E) may be used singly or may be used in combination.

Examples of the oil component for component (D) include triglycerides jojoba oil, olive oil, castor oil, and sunflower seed oil and the like, and the like.

The oil component for component (D) is desirably contained within the range of 0.05-5 wt %, preferably 0.1-3 wt %, more preferably 0.2-1.5 wt %, in the cleansing agent composition of the present invention.

Examples of the polyol for component (E) include propylene glycol, glycerol, butyleneglycol and the like.

The polyol for component (E) is desirably contained within the range of 0.1-30 wt %, preferably 0.15-25 wt %, more preferably 0.2-20 wt %, in the cleansing agent composition of the present invention.

The cleansing agent composition of the present invention can optionally contain other surfactants, for example, anionic surfactants such as alkyletheracetate, polyoxyethylene alkyl etheracetate and the like, nonionic surfactants such as fatty acid amide, polyoxyethylene alkyl ether, sugar ester, sugar ether, sugar amide and the like, and amphoteric surfactants such as imidazoline, betaine and the like in combination as long as the effect of the invention is not impaired.

As other additive, components generally used for cleansing agents can be optionally contained in combination as long as the effect of the invention is not impaired. For example, viscosity modifiers such as methylcellulose, ethanol, polyoxyethyleneglycol distearate and the like, pearly sheen agent, flavor, dye, UV absorber, antioxidant, antimicrobial agent, anti-inflammatory agent, preservative and the like can be added.

The cleansing agent composition of the present invention can be produced by a conventional method, and can take a dosage form of paste, gel, liquid, solid and the like. It is suitable as a cleansing agent for the body such as skin, hair and the like, and particularly preferable for washing skin.

EXAMPLES

The present invention is now explained in detail in the following by referring to Examples. However, the present invention is not limited to the Examples shown below.

The cleansing agent compositions described in the following Table 1 were prepared, and the cleansing agent compositions were evaluated for detergency, irritation, rough skin after washing and drying, softness after using the compositions, feeling of moisture after using the compositions, touch of skin after rinsing (smoothness), and suppression of separation and precipitation. As regards detergency, rough skin after washing and drying, softness after using the compositions, feeling of moisture after using the compositions, and touch of skin after rinsing (smoothness), sensory evaluation was performed by 10 male and female panelists. Evaluation of irritation was performed by 5 panelists often having rough hands as the target. When points were used for the evaluation, average was calculated by the following criteria and a mean of not less than 4.5 was judged to be very good (⊙), 3.5-4.4 to be good (◯), 2.5-3.4 to be normal (Δ), and 2.4 or below, to be failure (x)

Evaluation 1: Detergency

Commercially available soil (3 g, KANYO-NO-SUKINA-TSUCHI 5 L manufactured by NISSHIN) was placed on a palm, smear the palms of both hands with the soil, various cleansing agent compositions were taken by 1 mL in a syringe, tap water (3 mL) was added, and the both hands were rubbed as if to wash the palm surfaces for 30 seconds. The cleansing composition and the soil were washed away with running water (tap water), and the palm was visually observed. Evaluation was made by giving the following grades by using, as the standard, a previously-prepared photograph showing a level of stain removal.

5 points: stain was removed better than photograph.
4 points: stain was removed somewhat better than photograph.
3 points: same as photograph.
2 points: stain was removed somewhat less than photograph.
1 point: stain was removed less than photograph.

Evaluation 2: Irritation

By cooperation of 5 panelists having rather rough hands (skin surface seems to be more dried than in general people), the cleansing agent composition taken by 1 g in a syringe was used to wash both hands by gently rubbing them for 30 seconds, and the sense of stimulation to the hands was evaluated according to the following criteria.

⊙: Of 5 panelists, 5 evaluated absence of stimulation.
◯: Of 5 panelists, 4 evaluated absence of stimulation.
Δ: Of 5 panelists, 3 evaluated absence of stimulation.
x: Of 5 panelists, not more than 2 evaluated absence of stimulation.

Evaluation 3: Rough Skin after Washing and Drying

Various cleansing agent compositions were taken by 1 mL on hand by a syringe, tap water (3 mL) was added, and the both hands were rubbed as if to wash the palm surfaces for 30 seconds. The hands were rinsed with running water (tap water) and dried with a towel, and the evaluation was made 3 minutes later.

5 points: no feeling of dryness. Feeling of skin being stretched is absent.
4 points: Slight feeling of dryness. Skin is slightly stretched.
3 points: Feeling of dryness is felt. Skin is stretched.
2 points: Between 3 points and 1 point.
1 point: Considerable feeling of dryness is felt. Skin is considerably stretched.

Evaluation 4: Softness of Skin after Use

Various cleansing agent compositions were taken by 1 mL on hand by a syringe, tap water (3 mL) was added, and the both hands were rubbed as if to wash the palm surfaces for 30 seconds. The hands were rinsed with running water (tap water) and dried with a towel, and the evaluation was made 3 minutes later.

5 points: Felt to have become soft.
4 points: Felt to have become somewhat soft.
3 points: Same as before washing.
2 points: Felt to have become somewhat hard.
1 point: Felt to have become hard.

Evaluation 5: Feeling of Moisture of Skin after Use

Various cleansing agent compositions were taken by 1 mL on hand by a syringe, tap water (3 mL) was added, and the both hands were rubbed as if to wash the palm surfaces for 30 seconds. The hands were rinsed with running water (tap water) and dried with a towel, and the evaluation was made 3 minutes later.
5 points: Moist feeling is felt.
4 points: Moist feeling is felt somewhat.
3 points: Same as before washing.
2 points: Moist feeling became somewhat less than before washing.
1 point: Moist feeling became less than before washing.
Evaluation 6: Touch of Skin after Rinsing (Smoothness)
Various cleansing agent compositions were taken by 1 mL on hand by a syringe, tap water (3 mL) was added, and the both hands were rubbed as if to wash the palm surfaces for 30 seconds. The hands were rinsed with running water (tap water) and dried with a towel, and the evaluation was made 3 minutes later.
5 points: Skin surface is felt to have become smooth.
4 points: Skin surface is felt to have become somewhat smooth.
3 points: Same as before washing.
2 points: Smoothness of skin surface is felt to have become somewhat exacerbated than before washing.
1 point: Smoothness of skin surface is felt to have become exacerbated than before washing.
Evaluation 7: Suppression of Separation and Precipitation
After stirring at 50° C. for 30 min and leaving at room temperature for 24 hr, visual observation was performed.
⊙: No separation and precipitation.
○: No separation, and precipitation and suspended matter are not observed, but rather cloudy as a whole.
Δ: No separation, and precipitation and suspended matter are not observed, but cloudy as a whole.
x: Precipitation or suspended matter is observed.

TABLE 1

| | blended components | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| (A) | sodium polyoxyethylene lauryl ether sulfate | 25.0 | | | | 25.0 | 25.0 | 25.0 | 25.0 | 25.0 |
| | sodium lauryl sulfate | | 25.0 | | | | | | | |
| | disodium lauryl sulfosuccinate | | | 25.0 | | | | | | |
| | disodium polyoxyethylene lauryl sulfosuccinate | | | | 25.0 | | | | | |
| (B) | heterocyclic compound (R1 = R2 = hydrogen) | 0.1 | 0.1 | 0.1 | 0.1 | 0.1 | 0.1 | 0.1 | 0.1 | |
| | heterocyclic compound (R1 = R2 = methyl group) | | | | | | | | | 0.1 |
| (C) | (acrylates/(C10-30) alkyl acrylate) crosspolymer | | | | | | 0.5 | | | |
| | (acrylates/steareth-20 methacrylate) crosspolymer | | | | | | | 0.5 | 0.5 | 0.5 | 0.5 |
| (D) | jojoba oil | | | | | | | 1.0 | 1.0 | 1.0 |
| (E) | glycerol | | | | | | | | 3.0 | 3.0 |
| | purified water | balance | balance | balance | balance | balance | balance | balance | balance | balance |
| | evaluation 1: detergency | ⊙ | ⊙ | ⊙ | ⊙ | ⊙ | ⊙ | ⊙ | ⊙ | ⊙ |
| | evaluation 2: irritation | ○ | ○ | ○ | ○ | ○ | ○ | ⊙ | ⊙ | ⊙ |
| | evaluation 3: rough skin after washing and drying | ⊙ | ⊙ | ⊙ | ⊙ | ⊙ | ⊙ | ⊙ | ⊙ | ○ |
| | evaluation 4: softness of skin evaluation after use | ⊙ | ⊙ | ⊙ | ⊙ | ⊙ | ⊙ | ⊙ | ⊙ | ○ |
| | evaluation 5: feeling of moisture of skin after use | Δ | Δ | Δ | Δ | Δ | Δ | ○ | ○ | ○ |
| | evaluation 6: touch of skin after rinsing (smoothness) | ○ | ○ | ○ | ○ | ⊙ | ⊙ | ⊙ | ⊙ | ⊙ |
| | evaluation 7: suppression of separation and precipitation | ○ | ○ | ○ | ○ | ○ | ○ | Δ | ○ | ○ |

In the described Examples, detergency was satisfactory due to the use of various anionic surfactants. In addition, it was confirmed that the irritation, rough skin, moisture, and softness were of a level free of problem or a satisfactory level due to the addition of a heterocyclic compound. When polyacrylic acid, oil, and further, polyol were added, a cleansing agent composition showing satisfactory touch of skin and having ensured stability could be obtained.

The liquid cleansing agents shown below were prepared. All of them were compositions having high detergency, showing no stimulation, and free from rough skin after washing.

TABLE 2

Blending Example 1

| components | wt % |
| --- | --- |
| sodium cocoylisethionate | 10 |
| polyoxyethylene lauryl ether sulfate triethanolamine | 5 |
| heterocyclic compound (R1═R2═hydrogen) | 0.01 |
| acrylic acid-methacrylic acid alkyl copolymer (carbon number of alkyl group 10-30, molecular weight about 1,500,000) | 0.2 |
| carboxyvinyl polymer | 0.2 |
| 1,3-butyleneglycol | 4 |
| purified water | balance |

TABLE 3

Blending Example 2

| components | wt % |
| --- | --- |
| TEA lauryl sulfate | 15 |
| heterocyclic compound (R1═R2═hydrogen) | 0.005 |
| lauryl dimethylamineoxide | 1 |
| coconut oil fatty acid diethanolamide | 2 |
| cationic cellulose | 0.5 |
| glycerol | 4 |
| sunflower seed oil | 0.5 |
| ethylene glycol distearate | 1.5 |
| tetrasodium hydroxyethane diphosphonate | 0.8 |
| coconut oil fatty acid sodium | 1 |
| purified water | balance |

The details of the compounds used are as described below.
heterocyclic compound (R1=R2=hydrogen): manufactured by Tokyo Chemical Industry Co., Ltd.
heterocyclic compound (R1=R2=methyl group): manufactured by Bachem Inc.
sodium polyoxyethylene lauryl ether sulfate: EMAL 20C manufactured by Kao Corporation
sodium lauryl sulfate: EMAL 0 manufactured by Kao Corporation disodium lauryl sulfosuccinate: Kohakuru L-40 manufactured by TOHO Chemical Industry Co., Ltd.
polyoxyethylene disodium lauryl sulfosuccinate: RIKAMILD ES-100 manufactured by New Japan Chemical Co., Ltd.
(acrylates/(C10-30) alkyl acrylate) crosspolymer: carbopol EDT 2020 manufactured by Nikko Chemicals
(acrylates/steareth-20 methacrylate) crosspolymer: ACU-LYN 88 manufactured by Rohm and Haas Inc.
jojoba oil: NIKKOL jojoba oil S manufactured by Nikko Chemicals
glycerol: glycerol 85 manufactured by NOF CORPORATION

INDUSTRIAL APPLICABILITY

The composition obtained by the present invention has high detergency and low irritativeness, can suppress rough skin after washing and drying, and surprisingly, confers softness and moisture to the skin after use, can improve touch of skin after rinsing, and is also superior in stability.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cleansing agent composition, comprising:
   (A) at least one surfactant selected from the group consisting of a sulfonate surfactant, a sulfate anionic surfactant, and a mixture thereof; and
   (B) at least one heterocyclic compound represented by formula (1):

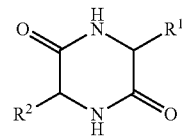

(1)

wherein $R^1$ and $R^2$ are each independently a hydrogen atom, a methyl group, a hydroxymethyl group, or a hydroxyethyl group.

2. A cleansing agent composition according to claim 1, wherein $R^1$ and $R^2$ are both hydrogen atoms.

3. A cleansing agent composition according to claim 1, wherein said sulfate anionic surfactant is an alkyl or alkenyl sulfate anionic surfactant.

4. A cleansing agent composition according to claim 2, wherein said sulfate anionic surfactant is an alkyl or alkenyl sulfate anionic surfactant.

5. A cleansing agent composition according to claim 1, which comprises (A) said at least one surfactant and (B) said at least one heterocyclic compound in a weight ratio (A/B) of (A) said at least one surfactant to (B) said at least one heterocyclic compound of 1000/10 to 1000/1.

6. A cleansing agent composition according to claim 2, which comprises (A) said at least one surfactant and (B) said at least one heterocyclic compound in a weight ratio (A/B) of (A) said at least one surfactant to (B) said at least one heterocyclic compound of 1000/10 to 1000/1.

7. A cleansing agent composition according to claim 3, which comprises (A) said at least one surfactant and (B) said at least one heterocyclic compound in a weight ratio (A/B) of (A) said at least one surfactant to (B) said at least one heterocyclic compound of 1000/10 to 1000/1.

8. A cleansing agent composition according to claim 4, which comprises (A) said at least one surfactant and (B) said at least one heterocyclic compound in a weight ratio (A/B) of (A) said at least one surfactant to (B) said at least one heterocyclic compound of 1000/10 to 1000/1.

9. A cleansing agent composition according to claim 1, which comprises (A) said at least one surfactant and (B) said at least one heterocyclic compound in a total amount of 5 to 95 wt %, based on the total weight of said cleansing agent composition.

10. A cleansing agent composition according to claim 2, which comprises (A) said at least one surfactant and (B) said at least one heterocyclic compound in a total amount of 5 to 95 wt %, based on the total weight of said cleansing agent composition.

11. A cleansing agent composition according to claim 3, which comprises (A) said at least one surfactant and (B) said at least one heterocyclic compound in a total amount of 5 to 95 wt %, based on the total weight of said cleansing agent composition.

12. A cleansing agent composition according to claim 4, which comprises (A) said at least one surfactant and (B) said at least one heterocyclic compound in a total amount of 5 to 95 wt %, based on the total weight of said cleansing agent composition.

13. A cleansing agent composition according to claim 1, further comprising:
(C) at least one polyacrylic acid or a derivative thereof.

14. A cleansing agent composition according to claim 2, further comprising:
(C) at least one polyacrylic acid or a derivative thereof.

15. A cleansing agent composition according to claim 3, further comprising:
(C) at least one polyacrylic acid or a derivative thereof.

16. A cleansing agent composition according to claim 4, further comprising:
(C) at least one polyacrylic acid or a derivative thereof.

17. A cleansing agent composition according to claim 1, further comprising at least one component selected from the group consisting of:
(D) an oil component;
(E) a polyol; and
(F) a mixture of an oil component and a polyol.

18. A cleansing agent composition according to claim 2, further comprising at least one component selected from the group consisting of:
(D) an oil component;
(E) a polyol; and
(F) a mixture of an oil component and a polyol.

19. A method of cleansing skin or hair, comprising contacting skin or hair with an effective amount of a cleansing agent composition according to claim 1.

20. A method of cleansing skin or hair, comprising contacting skin or hair with an effective amount of a cleansing agent composition according to claim 2.

* * * * *